United States Patent
Comparat et al.

(10) Patent No.: US 12,329,184 B2
(45) Date of Patent: Jun. 17, 2025

(54) METHOD FOR SUPPLYING WATER IN THE REARING OF LIVESTOCK AND DEVICE FOR PRODUCING BLOCKS OF AN AQUEOUS GEL

(71) Applicant: YNSECT, Evry (FR)

(72) Inventors: Solene Comparat, Evry (FR); Loïc Clesse, Roisel (FR); Thibault Du Jonchay, Chevrières (FR); Thomas Lefebvre, Soisy sur Seine (FR); Fabrice Berro, Paris (FR); Nathalie Berezina, Paris (FR); Clementine Seguimbraud, Baupte (FR)

(73) Assignees: YNSECT, Evry-Courcouronnes (FR); CARGILL, INCORPORATED, Wayzata, MN (US)

( * ) Notice: Subject to any disclaimer, the term of this patent is extended or adjusted under 35 U.S.C. 154(b) by 1380 days.

(21) Appl. No.: 16/474,100

(22) PCT Filed: Dec. 28, 2017

(86) PCT No.: PCT/EP2017/084784
§ 371 (c)(1),
(2) Date: Jun. 27, 2019

(87) PCT Pub. No.: WO2018/122361
PCT Pub. Date: Jul. 5, 2018

(65) Prior Publication Data
US 2020/0120897 A1    Apr. 23, 2020

(30) Foreign Application Priority Data
Dec. 29, 2016    (FR) ...................................... 1663522

(51) Int. Cl.
| | | |
|---|---|---|
| *A23K 50/90* | (2016.01) | |
| *A01K 67/30* | (2025.01) | |
| *A23K 10/00* | (2016.01) | |
| *A23N 17/00* | (2006.01) | |
| *C02F 1/68* | (2023.01) | |

(52) U.S. Cl.
CPC .............. *A23K 50/90* (2016.05); *A01K 67/30* (2025.01); *A23K 10/00* (2016.05); *A23N 17/00* (2013.01); *C02F 1/68* (2013.01)

(58) Field of Classification Search
CPC .... A23K 10/38; A23K 20/163; A23K 20/174; A23K 50/90; A23K 10/18; A23K 10/28;
(Continued)

(56) References Cited

U.S. PATENT DOCUMENTS

| | | |
|---|---|---|
| 5,643,622 A | 7/1997 | Sawhill |
| 6,293,223 B1 | 9/2001 | Blossey et al. |

(Continued)

FOREIGN PATENT DOCUMENTS

| | | | |
|---|---|---|---|
| FR | 2157819 | * | 6/1973 |
| FR | 2157819 A1 | | 6/1973 |

(Continued)

OTHER PUBLICATIONS

Chef Andy (2014, https://web.archive.org/web/20140219152804/http://www.chefandy.com/tips.html) (Year: 2014).*

(Continued)

*Primary Examiner* — Emily M Le
*Assistant Examiner* — Carrie Glimm
(74) *Attorney, Agent, or Firm* — Panitch Schwarze Belisario & Nadel LLP; Erin M. Dunston

(57) ABSTRACT

The invention relates to a method for producing blocks of an aqueous gel, comprising: a step of forming a compound by mixing: i. an aqueous substrate; and ii. the gelling agent, —a step of drawing off the compound; —a step of in-line cooling of the compound so as to bring it below a second temperature at which it gels; —a step of transferring to a distribution line; —a step of cutting the gelled compound into blocks at the outlet of the distribution line; and—a step of distributing the blocks of gel into a farming container
(Continued)

immediately after the gel is cut into blocks. Such a method allows blocks of gel to be produced continuously and as required in the context of rearing livestock, in particular rearing insects. The invention also relates to a corresponding device.

4 Claims, 2 Drawing Sheets

(58) Field of Classification Search
CPC ........ A23K 10/33; A23K 10/00; A23K 10/37; A23K 20/30; A23K 40/00; A01K 67/033; A01K 5/0216; A01K 29/00; A23N 17/00; A23N 17/005; A23N 17/007; C02F 1/22; C02F 1/68; A23P 30/00; A23L 29/20; B01J 13/0052
See application file for complete search history.

(56) References Cited

U.S. PATENT DOCUMENTS

| | | |
|---|---|---|
| 2009/0285937 A1 | 11/2009 | Vadis et al. |
| 2017/0251700 A1* | 9/2017 | Doane .................. A23K 20/10 |

FOREIGN PATENT DOCUMENTS

| | | | | |
|---|---|---|---|---|
| JP | 200060451 A | | 2/2000 | |
| JP | 2003219761 A | * | 8/2003 | |
| RU | 2300541 C2 | | 6/2007 | |
| WO | 0226048 A2 | | 4/2002 | |
| WO | WO-2015087299 A1 | * | 6/2015 | ............... A23K 1/14 |
| WO | 2016004312 A1 | | 1/2016 | |

OTHER PUBLICATIONS

ProSonix (2016, https://web.archive.org/web/20161130183504/https://www.pro-sonix.com/ap-41-food-jacketed-kettle-heating/) (Year: 2016).*
Millipore Sigma (Corn Steep Liquor, https://www.sigmaaldrich.com/US/en/product/sigma/c4648) (Year: 2023).*
International Search Report (PCT/ISA/210) issued on Mar. 19, 2018, by the European Patent Office as the International Searching Authority for International Application No. PCT/EP2017/084784.
Written Opinion (PCT/ISA/237) issued on Mar. 19, 2018, by the European Patent Office as the International Searching Authority for International Application No. PCT/EP2017/084784.

* cited by examiner

METHOD FOR SUPPLYING WATER IN THE REARING OF LIVESTOCK AND DEVICE FOR PRODUCING BLOCKS OF AN AQUEOUS GEL

The present invention relates to a method and a device for producing an aqueous gel in blocks.

It applies in particular to animal rearing farms, and preferably to insect rearing farms.

The insects to which the invention relates are for example the *Coleoptera, Diptera, Lepidoptera, Isoptera, Orthoptera, Hymenoptera, Blattoptera, Hemiptera, Heteroptera, Ephemeroptera* and *Mecoptera*, preferably the *Coleoptera, Diptera, Orthoptera*, and *Lepidoptera*.

The term "insect" is used to denote any stage of development from the egg or *ootheca* to the adult insect, and the invention relates more particularly to the rearing of insects from the larval stage to the adult insect.

Rearing of insects requires a supply of water and nutrients necessary for the insects' survival as well as their growth and proper development. Supplying all or part of the food and water in the form of a gelled aqueous compound is known.

For example, document U.S. Pat. No. 6,293,223 discloses a gelled nutrient medium for rearing larvae.

In the known examples, nutrients, for example solid nutrients, are mixed with water and a gelling agent such as agar at a suitable temperature. The compound obtained is gelled by cooling it to a lower temperature.

The gelled compound thus obtained is then cut into blocks of a suitable size. The blocks are packed in order to be sent to a larvae rearing farm.

According to another known embodiment, the liquid compound is poured into a tray comprising cavities of a size corresponding to the blocks required, where it is cooled and gelled before removal from the cavities in the tray.

Such a gelled aqueous compound constitutes a source of food and water that is easy to use, does not require a particular distribution structure in the rearing containers or cages, and provides a water supply while limiting the risks of drowning of the animals, in particular insects. However, although the use of a gelled compound has many advantages in the context of an animal rearing farm, for example an insect rearing farm, it has drawbacks or risks connected in particular with transport, handling, and storage of the compound, which in each of these operations is susceptible to contamination, or development of moulds.

The invention aims to propose a method and a device making it possible to solve at least one of the aforementioned drawbacks.

Thus, the invention relates to a method for producing blocks of an aqueous gel, comprising:
a step of forming a compound by mixing:
  i. an aqueous substrate, liquid at ambient temperature, heated to a temperature allowing dissolution of a gelling agent; and ii. gelling agent,
a step of drawing off the compound;
a step of in-line cooling of the compound so as to bring it below a second temperature, at which it is gelled;
a step of transfer to a distribution line;
a step of cutting the gelled compound into blocks, on leaving the distribution line; and
a step of distribution of the blocks of gel in a rearing container, immediately following the cutting of the gel into blocks.

By gelling the compound in line, after withdrawal in liquid form, and by cutting it into blocks directly at the outlet of a distribution line, the gel is produced continuously as required. Handling of the gel and storage thereof (in the form of gel) are eliminated, which also eliminates the associated problems. The risks of contamination or of development of bacteria are greatly curtailed, as the gel is distributed immediately on leaving the distribution line (which is essentially closed), shortly after the compound was formed at a high temperature. Moreover, in the context of an animal rearing farm, for example an insect rearing farm, the size of the blocks leaving the line can be finely and continuously adjusted to the requirements.

In an embodiment of the invention, the method comprises, before the step of drawing off the compound, cooling said compound and holding it in a temperature range, below the temperature allowing dissolution of the gelling agent but sufficient to keep the compound in the liquid state, said temperature range allowing supplements liable to be degraded at the temperature allowing dispersion of the gelling agent to be added without degradation.

Cooling comprises for example adding water or an aqueous substrate at ambient temperature or at a temperature below ambient temperature, in order to bring the compound into the temperature range, and holding the compound at temperature comprises controlling the temperature by activation and stopping of a means for heating the compound.

The heating means used may be of the type with steam circulating in a double wall of a vat used for the dissolution step and for the step of holding at temperature, activation of the heating means comprising sending steam into the double wall.

For example, the temperature range in which the compound is held may be defined so as to keep the compound at a viscosity less than 10 000 cP. The temperature range for the step of holding at temperature may be defined by two limits selected respectively between 45° C. and said temperature allowing dissolution of the gelling agent.

In a possible variant of the method, the compound is in the gel state at below 40° C.

The temperature allowing dissolution of a gelling agent to which the aqueous substrate is heated may be comprised between 60° C. and 100° C., in particular between 60° C. and 95° C., for example of the order of 95° C. or of the order of 75° C.

The gelling agent used may comprise one or more elements selected from: agar-agar, carrageenan, guar gum, calcium alginate, chitosan, pectin, xanthan gum, carob gum, gellan gum.

The method may also comprise adding at least one supplement among vitamins, a probiotic, a preservative, and minerals.

The aqueous substrate used may be water or may comprise a liquid agro-industry coproduct and have a water content greater than 35% by weight, in particular a water content greater than 50% by weight, with respect to the total weight of gel.

The aqueous substrate may comprise at least one of the following coproducts of the agricultural or agri-food industry:
solubles from maize, wheat, peas, cassava, sugar beet, sugar cane;
distillers' solubles, in particular distillers' solubles from wheat, maize, peas, cassava;
vinasses;
molasses;
yeast creams;
whey.

The invention also relates to a device for producing blocks of an aqueous gel comprising:
- a vat comprising one or more dispersing devices;
- an inlet for an aqueous substrate that is liquid at ambient temperature, opening into the vat;
- means for monitoring and controlling the temperature in the vat;
- means for drawing off liquid contents from the vat;
- a metering system;
- an exchanger for cooling the liquid contents withdrawn from the vat;
- at least one distribution line at the exchanger outlet;
- a gel distributor arranged at the end of each distribution line and comprising a cutting device suitable for cutting a gel into blocks; and
- means for bringing an animal rearing container under the distributor.

In such a device, the metering system may comprise a positive-displacement pump, for example a piston-type metering pump. The device may for example comprise a positive-displacement pump for each distribution line.

The distributing device may comprise an automated cutting system (for example a solenoid valve) suitable for cutting the gel at the outlet of the distribution line.

The distribution line and the cutting device may be configured for making blocks of gel with a volume comprised between 30 and 1500 cm³.

The means for monitoring and controlling the temperature in the vat may comprise a temperature sensor in the vat.

The vat may comprise a double wall provided with a steam inlet between the two walls and a control valve on the steam inlet.

The device may also comprise:
- a first inlet of aqueous substrate at a first temperature comprising a control valve and a flowmeter; and
- a second inlet of aqueous substrate at a second temperature comprising a control valve and a flowmeter.

Other particular features and advantages of the invention will become clear from the description given below.

BRIEF DESCRIPTION OF THE SEVERAL VIEWS OF THE DRAWINGS

In the attached drawings, given as non-limitative examples:

FIG. 1 shows a logic diagram giving details of the succession of steps carried out in an embodiment of the invention. The embodiment shown comprises the essential steps of the method according to the invention as well as a certain number of steps specific to the embodiment shown.

Figure 1:
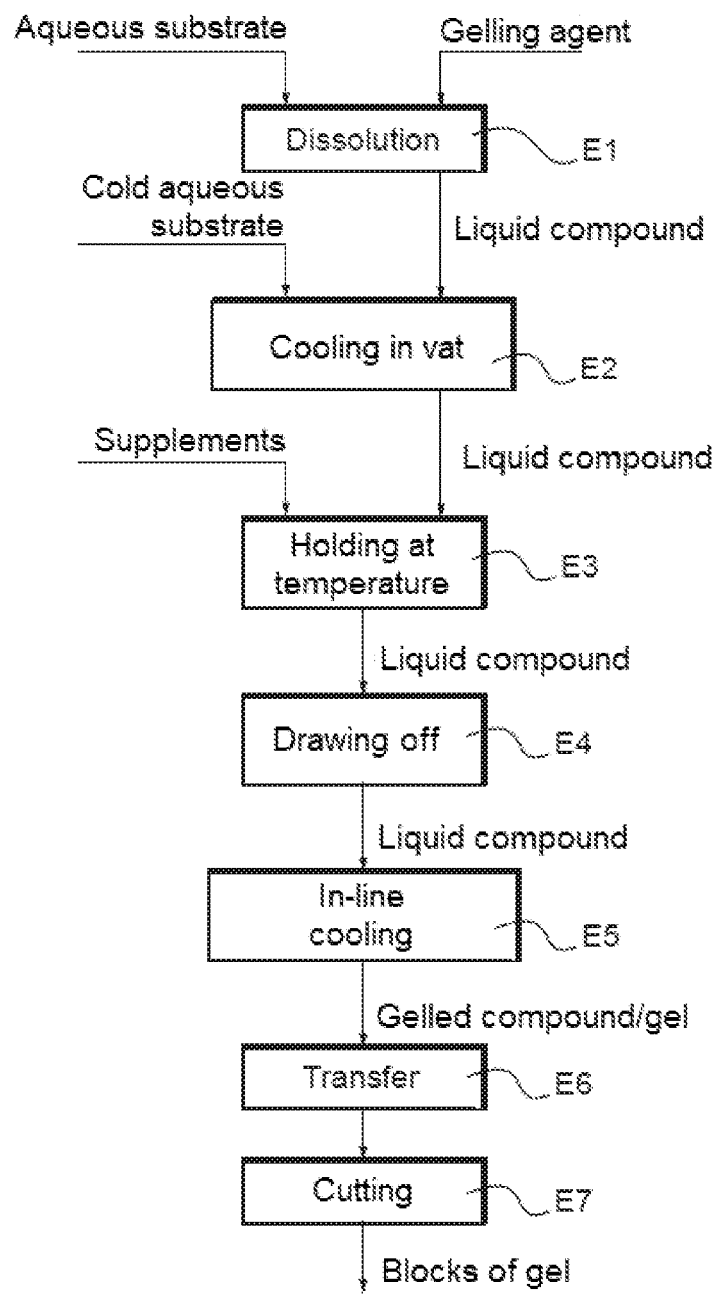
FIG. 1 shows diagrammatically a logic diagram of a method according to an embodiment of the invention.

An aqueous substrate, i.e. a product containing water, which is liquid at ambient temperature, is supplied. By "ambient temperature" is meant a temperature conventionally prevailing in a preparation workshop in the absence of heating or cooling of the premises. "Ambient temperature" may in particular denote a temperature comprised between 5° C. and 35° C. The concept of liquid comprises fluid products having a viscosity typically up to 10000 cP.

The aqueous substrate may be water. The aqueous substrate used may be a liquid containing at least 35% by weight water, and preferably between 55% and 98.2%. For example, the aqueous substrate used may be a liquid containing between 60% and 95%, and preferentially between 70% and 90% by weight water with respect to the total weight of aqueous substrate.

In particular, numerous agro-industry coproducts may be used. The aqueous substrate may for example be constituted by a mixture of water and an agro-industry coproduct. For example, the aqueous substrate may be constituted by water and at least 25% by weight, for example at least 50% by weight, for example 75% by weight, of agro-industry coproduct.

The gel produced may typically comprise:
- from 90 to 99.6% by weight of an aqueous substrate comprising at least 25% by weight with respect to the total weight of aqueous substrate, of a liquid coproduct from agro-industry,
- from 0.3 to 2% by weight of a gelling agent, and
- from 0.1 to 5% by weight of a preservative, the percentages by weight of aqueous substrate, gelling agent and preservative being expressed with respect to the total weight of the gel.

A coproduct is a material inevitably created during a process of manufacturing a product of interest.

In particular, the coproduct to which the invention relates is liquid. By "liquid" is meant that the coproduct is in liquid form at ambient temperature under normal conditions of atmospheric pressure. In particular, this means that it is a coproduct obtained directly at the end of an industrial process without carrying out any drying step.

More particularly, the liquid coproduct is an aqueous coproduct comprising soluble substances. Preferentially, the soluble substances present in the liquid coproduct are proteins and/or carbohydrates such as sucrose and/or lactose, more preferentially proteins and carbohydrates. The soluble substances may also comprise soluble fibres.

Advantageously, the liquid coproduct comprises at least 90% by weight soluble matter with respect to the total weight of dry matter.

By "agro-industry" is meant more particularly the industries for starch manufacture, potato starch manufacture, malting, bioethanol production, sugar production, fermentation, brewing, distilling and the dairy industry.

More particularly, the coproduct is an aqueous coproduct comprising soluble substances. Preferentially, the soluble substances present in the coproduct are proteins and/or carbohydrates such as sucrose and/or lactose, more preferentially proteins and carbohydrates. The soluble substances may also comprise soluble fibres.

The coproduct may also be or comprise a yeast cream, typically resulting from a process for producing bioethanol, or more generally from the fermentation industries. Yeast creams correspond to the coproducts resulting from separation of a wort such as by filtration or by centrifugation after fermentation. The fermentation industries also produce vinasses as a usable coproduct; these are liquid coproducts resulting from the fermentation of the wort after extraction of the compounds of interest.

The sugar industry generates several kinds of liquid coproducts that may be used, and in particular wash syrups and molasses. Wash syrups and molasses correspond to the syrupy residues obtained after crystallization of the liquor formed during sugar manufacture.

As a result, the liquid coproduct may be selected in particular from the list comprising: solubles from cereals, solubles from maize, solubles from wheat, solubles from peas, solubles from cassava, solubles from sugar beet, solubles from sugar cane, distillers' solubles from cereals, distillers' solubles from wheat, distillers' solubles from maize, distillers' solubles from peas, distillers' solubles from cassava, vinasses, molasses, yeast creams, whey and concentrated derivatives thereof, in particular permeate, or mixtures thereof.

The gel may comprise yeasts. The yeasts may be derived from the liquid agro-industry coproduct. The agro-industry coproduct may in fact be a distillers' soluble that already comprises yeasts or a mixture of at least two liquid agro-industry coproducts, one of which is a yeast cream.

Alternatively, the yeasts may be added in solid form, for example in the form of dry yeasts, as indicated below, as a probiotic. In the form of dry yeasts, they are introduced at a content comprised between 0.1 and 6% by weight, preferentially between 1 and 5% by weight with respect to the total weight of the gel.

The aqueous substrate is heated to a desired temperature, with a view to dissolution of a gelling agent in the aqueous substrate. The desired temperature may typically be comprised between 60° C. and 100° C., in particular of the order of 95° C., or of the order of 75° C., depending on the gelling agent used. The aqueous substrate is supplied at this temperature before being fed into a vat, or is brought to this temperature once in said vat.

In a dissolution step E1, a gelling agent is added to the aqueous substrate. The gelling agent may be, or may comprise, for example: agar-agar, carrageenan, guar gum, calcium alginate, chitosan, pectin, xanthan gum, carob gum, gellan gum or mixtures thereof.

As the aqueous substrate is at a sufficient temperature, the gelling agent dissolves in the aqueous substrate. At the temperature (which remains almost constant as the quantity of gelling agent added to the substrate is low as a proportion of said substrate) the compound thus formed is liquid.

In the dissolution step E1, mixing is carried out in order to obtain a liquid compound in which the gelling agent is distributed uniformly. Mixing is carried out in a suitable vessel, typically a vat.

A preservative may also be added, for example at a content comprised between 0.1 and 5% by weight of the gel obtained at the end of the process, preferentially between 0.15% and 0.5%, for example 0.3%. The preservative may be selected from the group constituted by acetic acid, sodium acetate, formic acid, sodium lactate, fumaric acid, sorbic acid, propionic acid, citric acid, potassium sorbate, calcium sorbate, sodium propionate, calcium propionate, sodium benzoate, benzoic acid, calcium benzoate, potassium benzoate, butyric acid, as well as the salts and acids corresponding to these molecules.

Preferably, the preservative is not a paraben.

The example of the method presented here comprises a cooling step E2 in the vat, during which the compound is brought to a temperature below the dissolution temperature of the gelling agent, but greater than the gelation temperature of the compound. Cooling may be obtained by adding a quantity of cold aqueous substrate that allows the desired temperature to be reached. A cold aqueous substrate corresponds to the aqueous substrate at ambient temperature or at a lower temperature. The cold aqueous substrate is preferably in the liquid state. The aqueous substrate added is preferentially the same, i.e. of the same composition, as the substrate already present in the compound. It may be water.

Mixing of the compound in order to ensure uniformity (both in its composition and in its temperature) is continued throughout the cooling step E2 in the vat.

The quantity of cold aqueous substrate added for cooling in the vat is evaluated or established beforehand, so that it is taken into account when adding gelling agent for the dissolution step E1, so that the compound contains a proportion of gelling agent within a predetermined range, after the cooling step E2.

Typically, the final compound (after adding optional supplements as detailed in step E3 described below) may comprise between 0.3% and 2% by weight of gelling agent. For example, a gel based on water gelled with a gelling agent of xanthan-carob in equal parts may advantageously comprise between 0.3% and 0.8% by weight gelling agent.

The content of gelling agent in the compound will have an effet on the force of the gel finally obtained. Thus, in the context of an animal rearing farm, and in particular an insect rearing farm, and depending on the stage of development of the insects for which the gel is intended, a gel having a force of at least 30 g/cm$^2$, in particular between 30 g/cm$^2$ and 150 g/cm$^2$, for example of the order of 50 g/cm$^2$ or of the order of 80 g/cm$^2$ (at ambient temperature, for example at 20° C.) may advantageously be used. Thus, the gel is not sticky or adhesive. The insects can therefore move about on top of the gel without getting stuck. This therefore reduces insect mortality, fewer insects becoming trapped in the gel. Furthermore, the syneresis of the gel may advantageously be comprised between 0.1 and 5% to avoid excessive release of water and to moisten the insects' environment. The syneresis of the gel may be determined, for example as indicated in G. BLANCHER (2009), Sciences du Vivant [Life Sciences], ENSIA (AgroParisTech). Measurement is carried out on products stored at 4° C. for 24 h, by differential weighing with an analytical balance. Briefly, the product contained in a cup is weighed, then the surface liquid content is removed by tilting the cup, then with absorbent paper placed lightly on the surface of the product. A second weighing is then carried out. The syneresis is expressed as the percentage loss between the two weighings.

After the cooling step E2, the liquid compound is held at a set temperature, or in a desired temperature range, in a step of holding at temperature E3.

This temperature control may be carried out by activation (i.e. operation) of heating means when the compound cools down and could leave the control temperature range, and stopping said heating means when the compound warms up again and could leave the control temperature range.

Mixing of the compound with a view to guaranteeing its uniformity (both with respect to its composition and its temperature) is continued throughout the step of holding at temperature E3.

The control temperature range is selected so as to keep the compound in a liquid state, for example at a viscosity less than 10000 cP. The temperature range is also selected, if applicable, to allow addition to the compound of supplements that may be degraded by an excessive temperature, without degrading said supplements. The supplements added during the step of holding at temperature E3 are for example vitamins, a probiotic, a preservative, or a mixture of such supplements, or any other heat-sensitive compound of interest for nutritional formulation. For example, a probiotic may be added at a content comprised between 0.1% and 8% by weight (for example between 1% and 5%) of the gel obtained at the end of the method, and/or vitamins added in the form of a "premix" (which may also contain minerals and trace elements) with a content of "premix" between 0.1% and 5% by weight of the gel obtained at the end of the method. The minerals and/or the trace elements may alternatively be added independently of a premix or in addition to a premix. In particular, the vitamins added may be selected from vitamin A, vitamin B1 (thiamine), vitamin B2 (riboflavin), vitamin B3 (nicotinamide), vitamin B5 (pantothenic acid), vitamin B6 (pyridoxine), vitamin B8 (biotin), vitamin B9 (folic acid), vitamin B12 (cobalamin), vitamin PP (niacin), vitamin D3 (cholecalciferol), vitamin E, vitamin K3 (menadione), precursors thereof and derivatives thereof.

For example, a temperature range comprised between 45° C. and 65° C. is generally suitable. Any range comprised within these boundaries, for example a range from 50° C. to 60° C. may be envisaged. The narrower the range, the finer the temperature control must be.

The compound that is liquid at the holding (or control) temperature is then drawn off from the vat (or other vessel) in which it formed, and is distributed and pumped using one or more metering pumps in one or more lines, in a drawing off E4 and metering step.

The liquid compound is then gelled by cooling in a step of in-line cooling E5. The step of in-line cooling brings the compound to a below its gelation temperature, which may be for example of the order of 40° C. More generally, the compound thus gelled is brought to a temperature compatible with the use for which it is intended. For example, for feeding and supplying water to insects, the compound, which will be distributed at a temperature close to its temperature after in-line cooling E5, is brought to a maximum temperature of 25° C. at the outlet from in-line cooling E5.

The in-line cooling E5 may be carried out once, or in several stages of cooling, by gradual and successive cooling.

The gel thus obtained is transferred, in a transfer step E6, to a gel distribution line. The distribution line conveys the gel to its point of use. For example, for distribution of gel for feeding or supplying water to insects, the distribution line opens for example into or above rearing containers, which are advantageously brought successively to the outlet of the distribution line.

At the outlet or just before the outlet of a distribution line, the gel conveyed in the distribution line is cut into blocks, in a cutting step E7. The gel is thus distributed in the form of blocks of gel. The gel distributed may be used immediately.

The volume of the blocks depends on the intended use thereof. In the context of an animal rearing farm, in particular an insect rearing farm, blocks of gel having a volume comprised between 30 cm$^3$ and 1500 cm$^3$ may for example be produced. The blocks may have the shape of a parallelepiped (for example a cube, or a parallelepiped with a square base), or a cylinder, the length of which is of the order of 0.5 to 15 cm, preferentially 0.8 to 12 cm.

Figure 2:
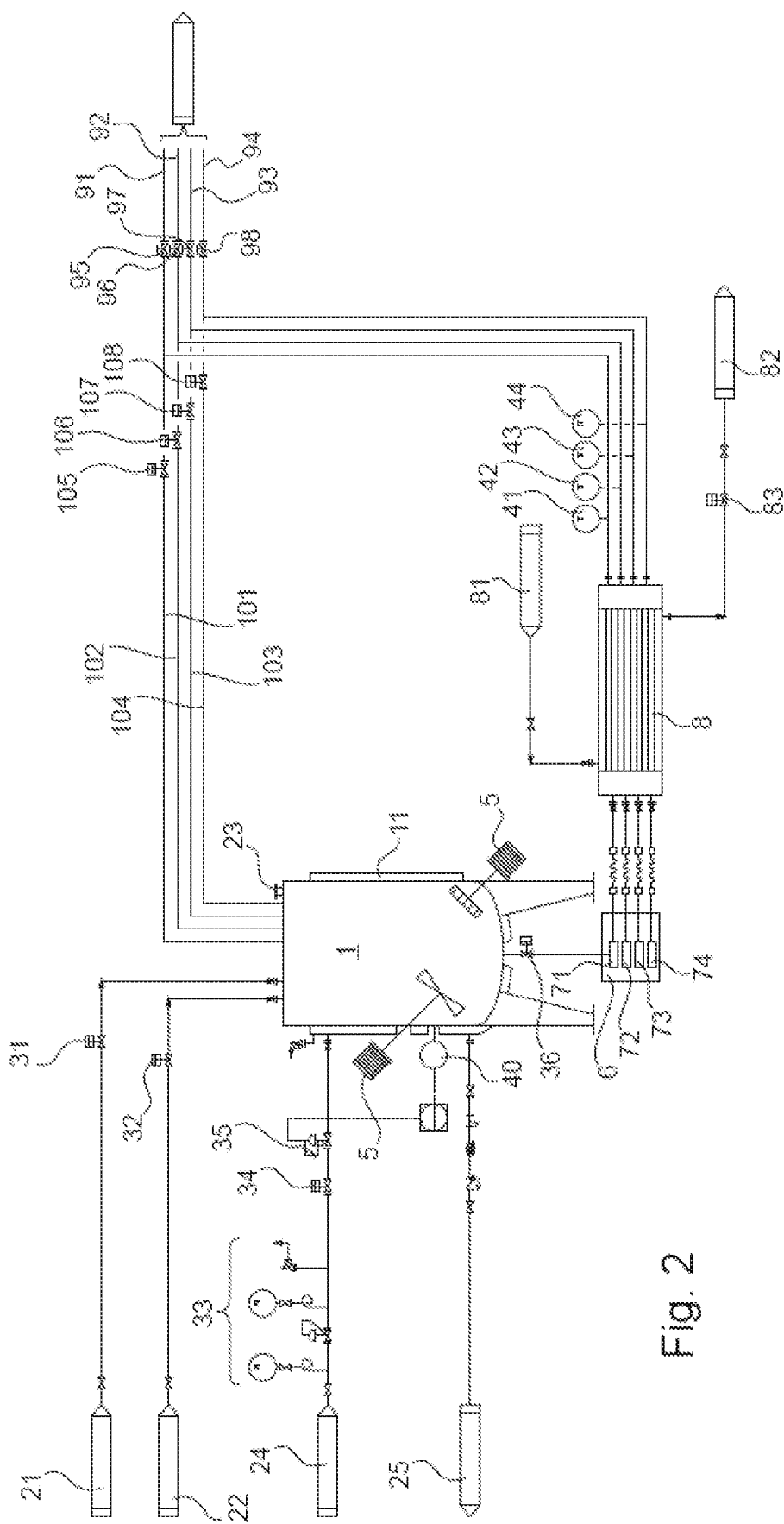
FIG. 2 shows diagramatically a device for implementing a method according to an embodiment of the invention.

FIG. 2 shows schematically an industrial device for implementing the method described above.

The device comprises a vat 1.

The vat 1 is fed by:
an inlet of cold aqueous substrate 21, for example water, at or below ambient temperature. The inlet of cold aqueous substrate 21 is provided with an inlet valve of cold aqueous substrate 31, which may be a control valve, and
an inlet of hot aqueous substrate 22, for example water. The inlet of hot aqueous substrate 22 is provided with an inlet valve of cold aqueous substrate 32, which may be a control valve. The hot aqueous substrate is at a temperature allowing dissolution of a gelling agent, for example of the order of 75° C.

The vat also comprises an inlet 23 for feeding additional products into the vat 1. The inlet 23 may be used for example for adding a gelling agent or supplements.

The vat 1 is of the double-wall type, providing a space 11 between the walls of the vat 1. A steam inlet 24 opens into the space 11. The steam inlet 24 is provided with a certain number of control devices 33, in particular for controlling the pressure of the steam. The steam inlet 24 is provided with a steam inlet valve 34, which may be a control valve. The steam inlet 24 is also provided with a control valve 35, the opening of which is controlled as a function of the temperature of the compound in the vat. For this purpose, and if applicable for controlling other functions, a temperature sensor in the vat 40 makes it possible to measure the temperature of the compound in the vat. Several temperature sensors in the vat may be provided and distributed spatially in the vat, to avoid scatter of measurements and in addition ensure good uniformity of the temperature of the compound in the vat.

By controlling the control valve 35 it is thus possible for example to control the temperature of the compound present in the vat, i.e. hold it at a set temperature or in a predefined temperature range.

The steam inlet 24 is advantageously located at the top of the vat.

The vat 1 is also provided with an outlet for condensates 25 resulting from the steam cooled and condensed following heat transfer to the inside wall of the vat 1 and to the compound that it contains.

In an embodiment that is not shown, the double jacket of the vat 1 may be configured for receiving, in the same space as the steam or in a dedicated space, cold water for cooling the contents of the vat 1.

The vat 1 is provided with at least one dispersing device 5. In the example shown here, the vat 1 is provided with two dispersing devices 5. The dispersing devices 5 allow mixing of the compound present in the vat 1, and quick and uniform dispersion of any product, liquid or pulverulent, added to the compound.

A draw-off valve 36, located on a discharge line at the bottom of the vat 1, allows drawing off of the compound present in the vat 1. A hopper 6 is configured for distributing the drawn-off compound into several lines. Of course, the number of lines depends on the variant of the invention considered, and the invention also relates to a device only comprising a single line.

Each line is provided with a positive-displacement pump, or metering pump. The metering pump used must allow the compound to be pumped in the line firstly in liquid form, and then in the form of gel. A piston pump is particularly suitable for this.

In the example shown here, the device comprises four lines after the hopper 6: a first line is equipped with a first metering pump 71, a second line is equipped with a second metering pump 72, a third line is equipped with a third metering pump 73, and a fourth line is equipped with a fourth metering pump 74.

The compound, still liquid in each of the lines, then passes through an exchanger 8.

The exchanger 8 is of the liquid/liquid type. It cools the compound by circulating a cold liquid, typically water, around a tube bundle in which the compound is conveyed. The exchanger 8 comprises a cooling water inlet 81 and a water outlet 82.

The exchanger 8 makes it possible to bring the compound to below its gelation temperature. Thus, the compound leaves the exchanger 8 in the form of a gel, at the desired temperature for its distribution (or close to the desired temperature). A cooling water outlet valve 83 may allow the flow of water in the exchanger 8 to be stopped. In a variant of the invention, the water outlet valve 83 may be a control valve, making it possible to control the temperature of the gel at the outlet of the exchanger 8 by controlling the flow of water passing through the exchanger 8.

The cooling water may circulate in a closed loop and may be cooled before it is brought back to the water inlet 81.

In variants of the invention that are not shown, the exchanger 8 may be replaced with a succession of exchangers in series. In addition, each line could be equipped with its own exchanger.

In order to control the temperature of the gel leaving the exchanger 8, each line is equipped with a temperature sensor in the line. The device thus comprises a temperature sensor in the first line 41, a temperature sensor in the second line 42, a temperature sensor in the third line 43, and a temperature sensor in the fourth line 44.

The compound in the form of gel is then transferred to a distribution line, or to a return line to the vat. The device shown here comprises four distribution lines: a first distribution line 91, a second distribution line 92, a third distribution line 93 and a fourth distribution line 94. The device shown here comprises four return lines to the corresponding vat: a first return line 101, a second return line 102, a third return line 103 and a fourth return line 104.

Each distribution line is equipped with a gel distributor arranged at the end of the line. The gel distributor comprises in particular a cutting device suitable for cutting a gel into blocks. The cutting device may comprise a valve, in particular of the "stop-drop" type, allowing the gel to be cut cleanly. The cutting device may in particular be an automated cutting system. The automated cutting system may typically be pneumatic or electrical. For example, the first distribution line 91 comprises a first solenoid valve 95, the second distribution line 92 comprises a second solenoid valve 96, the third distribution line 93 comprises a third solenoid valve 97 and the fourth distribution line 94 comprises a fourth solenoid valve 98. At the outlet of the distribution line, the distributor thus supplies blocks of gel, of fixed or variable volume, the volume being determined by the length of gel delivered by a line before cutting.

The return lines allow the compound to return to the vat 1. Such return may be necessary when initiating drawing-off. In fact, during initiation, this closed-loop circulation may make it possible to remove the air present in the lines of the device. Furthermore, during initiation the gel may have a temperature that is too high at the outlet of the exchanger 8. Return of compound to the vat 1 may also be necessary when, for whatever reason, the quantity of compound dispensed into a line is greater than the quantity to be distributed. Return of compound to the vat 1 may also be necessary when circulation of the compound is desired in a line, whereas its distribution is not desired. This may for example be the case if distribution of gel is desired at a given temperature greater than ambient temperature, and if the compound remains in the lines for too long its temperature would be too low for it to be distributed. Finally, return to the vat may be used, outside the phases of gel production, for cleaning the device. Return may be regulated by, respectively: a first return valve 105, a second return valve 106, a third return valve 107, and a fourth return valve 108.

In the context of an animal rearing farm, and in particular an insect rearing farm, the device may additionally be provided with means for bringing an animal rearing container under the distributor. Thus, the distributor makes it possible to deposit one or more blocks of gel, of predefined volume or adapted for each container, directly after production in the container, without additional handling of the gel.

The invention thus proposes the formation of a gel of an aqueous substrate, for example a water gel, produced in situ and continuously distributed on demand in the form of blocks. Handling of the gel and storage thereof are eliminated, effectively eliminating the associated problems, in particular of contamination or putrefaction. Moreover, in the context of an animal rearing farm, for example an insect rearing farm, the size of the blocks at the outlet may continuously be adapted to the requirements.

The invention claimed is:

1. A method of supplying water in an animal rearing farm, comprising:
    a step of forming a compound by mixing in a vat:
    i. an aqueous substrate that comprises a liquid agro-industry coproduct comprising at least one of:
        solubles selected from the group consisting of maize, wheat, peas, cassava, sugar beet, and sugar cane;
        distillers solubles;
        vinasses;
        molasses;
        yeast creams; and
        whey,
    and wherein the aqueous substrate has a water content greater than 35% by weight, is liquid at ambient temperature, and the aqueous substrate is brought to a temperature allowing the dissolution of a gelling agent; and
    ii. gelling agent,
        a step of cooling the compound and holding the compound in a temperature range below the temperature allowing dissolution of the gelling agent but sufficient to keep the compound in the liquid state,
        a step of adding at least one supplement selected from the group consisting of a vitamin, a probiotic, and a mineral, wherein the temperature range for the step of holding the compound in a temperature range is defined by two boundaries selected respectively between 45° C. and said temperature allowing dissolution of the gelling agent;
        a step of drawing off the compound from the vat;
        a step of in-line cooling of the compound in at least one exchanger so as to bring the compound below a second temperature, to form a gelled compound;
        a step of transfer of the gelled compound to a distribution line;
        a step of cutting the gelled compound into blocks, at the outlet of the distribution line; and
        a step of distribution of the blocks of gel in a rearing container containing the animals, immediately following cutting of the gel into blocks, the step of distribution comprising bringing the rearing container containing the animals so that the distribution line opens into or above the rearing container.

2. The method according to claim 1, in which cooling is obtained by adding water at ambient temperature or at a temperature below ambient temperature into the compound in order to bring the compound into the temperature range or by adding aqueous substrate at ambient temperature or at a temperature below ambient temperature into the compound in order to bring the compound into the temperature range, and, the vat being a double walled vat, wherein holding the compound at temperature consists of controlling the temperature by sending steam into the double wall of the vat and stopping sending steam into the double wall of the vat.

3. The method according to claim 1, in which the temperature allowing dissolution of a gelling agent, to which the aqueous substrate is heated, is between 60° C. and 100° C.

4. The method according to claim 1, in which the gelling agent comprises one or more elements selected from: agar-agar, carrageenan, guar gum, calcium alginate, chitosan, pectin, xanthan gum, carob gum, or gellan gum.

* * * * *